Aug. 19, 1975 P. ECKE, JR Plant Pat. 3,766
POINSETTIA PLANT
Filed July 15, 1974
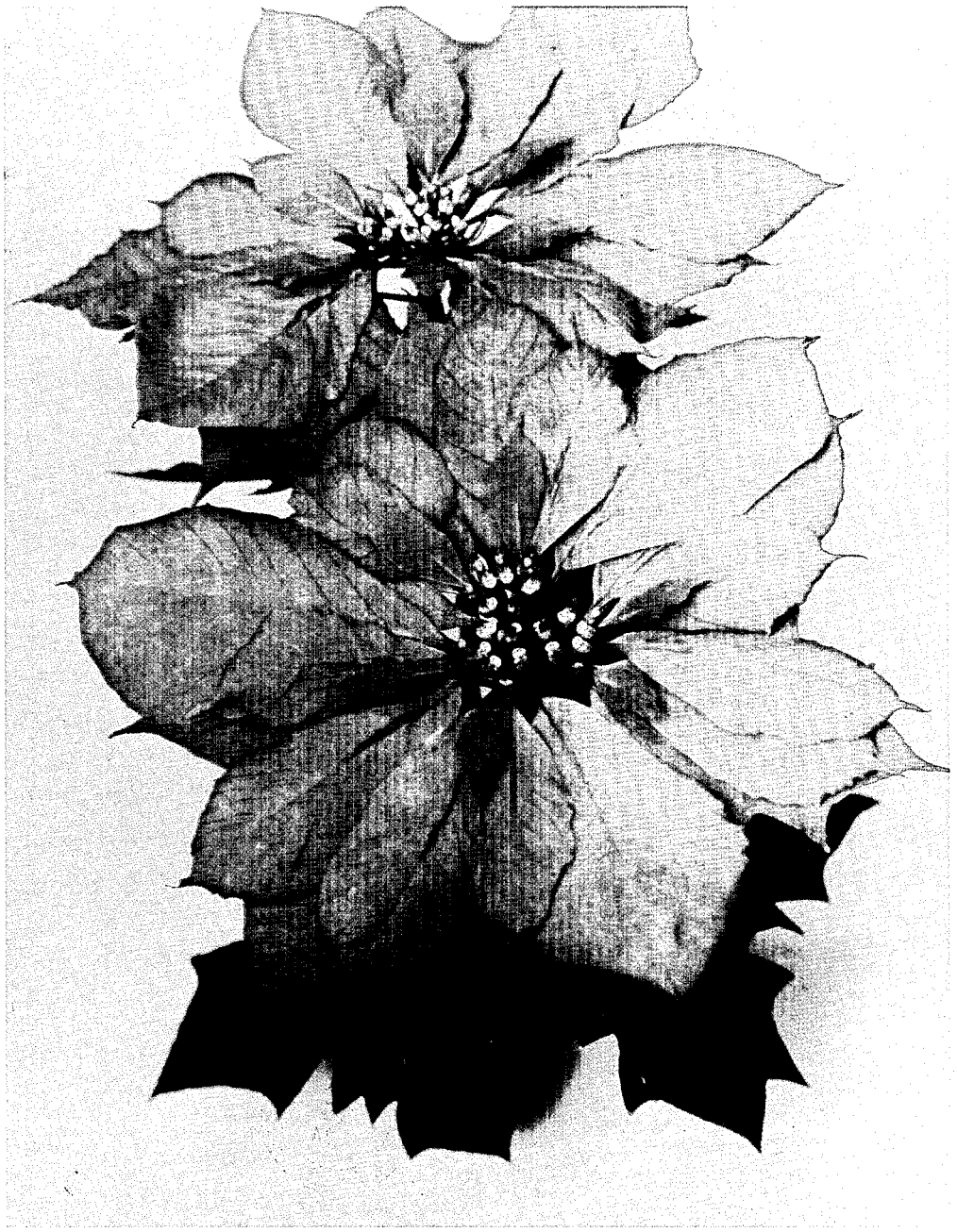

United States Patent

Plant Pat. 3,766

Patented Aug. 19, 1975

3,766

POINSETTIA PLANT

Paul Ecke, Jr., Encinitas, Calif., assignor to Paul Ecke Ranch, Encinitas, Calif.

Filed July 15, 1974, Ser. No. 488,328

Int. Cl. A01h 5/00

U.S. Cl. Plt.—86 1 Claim

ABSTRACT OF THE DISCLOSURE

A new and improved variety of red poinsettia plant distinguished by a medium tall growth habit and ability to bloom in 10 to 11 weeks under 3° to 4° lower night temperature than ordinarily required, the plant having a prolific production of bright red bracts which have a very erect horizontal appearance when mature and which provide a very full and long lasting effect for the plant when it is in full bloom.

*Background of the New Plant Variety*

My new variety of poinsettia plant originated as a seedling of unknown parentage produced as a result of extensive hybridizing efforts carried on by me and under my direction at Encinitas, Calif., with the object of developing new and improved varieties for the commercial trade. This new plant was discovered by me in the course of my study of a crop of seedlings produced by a multitude of crosses and I selected this plant for propagation and test because of its relatively higher growth habit and its luxurious appearance resulting from a profuse production of bright red bracts.

Asexual propagation of this plant in greenhouse under my direction, by means of cuttings, through successive generations has shown this plant to have its psysiological characteristics running true from generation to generation and to be firmly fixed. Propagation of this new variety of poinsettia plant is now being done for the commercial market by means of vegetative cuttings at Encinitas, Calif.

*Description of the Drawing*

My new variety of poinsettia plant is illustrated by the accompanying photographic drawing which shows bracts, flowers and foliage of the plant in full bloom, the color rendition being as nearly true as is reasonably possible to obtain by conventional photographic procedures.

*Description of the New Plant*

The following is a detailed description of my new variety poinsettia plant with color designations according to the R.H.S. Colour Chart published by the Royal Horticultural Society of London, England, in collaboration with the British Colour Council.

THE PLANT

Origin: Seedling.

Parentage: Unknown.

Classification:

- Botanic—*Euphorbia pulcherrima.*
- Commercial—Greenhouse poinsettia.

Height: Medium tall.

Growth Habit: Upright and vigorous, with sturdy stiff stems and a branching habit like that of Eckespoint C–1 Red (Plant Pat. 2,923).

Growth Rate: Very fast, rooting in 10 to 15 days under mist and blooming in 10 to 11 weeks at night temperatures 3 to 4° lower than required for Eckespoint C–1 during October, November and December.

Foliage: Alternate, horizontal, persistent and in normal abundance.

- Leaf Size: Medium. About 3 to 6 inches long and about 2½ to 5 inches wide.
- Leaf Shape: Ovate-acuminate with substantially entire margins having two dentations on each side.
- Aspect: Medium glossy and smooth upper side. Under side is dull with ordinary veining.
- Color: Dark Green RHS 147A on top and RHS 147B on under side. Generally similar to Eckespoint C–1 (P.P. 2,923).

Bracts: Number—15 to 20 in overlapping arrangement to provide a full effect.

- Size: Up to 6 inches long x 5 inches wide.
- Shape: Elliptic-acuminate with some serrations.
- Ribs and Veins: Mature bracts often have double vertically raised ridges extending about one-third the length of the bract from its junction with the petiole, these ridges being located one on each side of the main vein on the top side of the bract and are often as high as three-sixteenths of an inch. The veins on the under side are very pronounced and a very light green in color at all stages of bract maturity.
- Color: Bright red. Top side—RHS 45A to 45B; under side—RHS 45C.
- Retention: Long lasting with characteristics similar to Eckespoint C–1 (P.P. 2,923).

In general, this new variety of poinsettia plant is very similar to Eckespoint C–1 Red, in most of its characteristics, such as rooting time, branching ability, leaf retention and production of cuttings, as described in my Plant Pat. 2,923. The outstanding distinction and advantage of this new variety, however, resides in its somewhat taller growth habit and its ability to grow at 3 to 4° lower night temperature than Eckespoint C–1 to bloom in 10 to 11 weeks. This capability provides a very special commercial value for this new variety in that it produces large luxury-type plants with a very substantial saving of the fuel required for greenhouse heat.

I claim:

1. A new and distinct variety of poinsettia plant substantially as herein shown and described, characterized by its ability to grow at 3 to 4 degrees lower night time temperature than prior varieties to produce large luxury-type plants for the commercial trade.

No references cited.

ROBERT E. BAGWILL, Primary Examiner